(12) United States Patent
Rehberger et al.

(10) Patent No.: US 7,384,628 B2
(45) Date of Patent: Jun. 10, 2008

(54) LACTIC ACID BACTERIA AND ITS USE IN DIRECT-FED MICROBIALS

(75) Inventors: Thomas G. Rehberger, Wauwatosa, WI (US); Elizabeth A. Galbraith, Wauwatosa, WI (US)

(73) Assignees: Agtech Products, Inc., Waukesha, WI (US); Merrick's, Inc., Middleton, WI (US)

(*) Notice: Subject to any disclaimer, the term of this patent is extended or adjusted under 35 U.S.C. 154(b) by 357 days.

(21) Appl. No.: 10/874,777

(22) Filed: Jun. 23, 2004

(65) Prior Publication Data
US 2005/0002921 A1 Jan. 6, 2005

Related U.S. Application Data

(60) Provisional application No. 60/480,663, filed on Jun. 23, 2003.

(51) Int. Cl.
- A23K 97/04 (2006.01)
- A23L 1/28 (2006.01)
- A23L 1/31 (2006.01)
- A01N 63/00 (2006.01)
- C12N 1/02 (2006.01)
- C12N 1/20 (2006.01)

(52) U.S. Cl. .......... 424/93.4; 424/93.3; 424/93.45; 426/2; 426/53; 426/54; 426/56; 426/61; 426/807; 435/252.9; 435/261; 435/855

(58) Field of Classification Search ............ None
See application file for complete search history.

(56) References Cited

U.S. PATENT DOCUMENTS

| | | | |
|---|---|---|---|
| 3,932,670 A | 1/1976 | Sakurai | |
| 3,956,482 A | 5/1976 | Hahn et al. | |
| 3,984,575 A | 10/1976 | Farr | |
| 4,579,734 A | 4/1986 | Hata et al. | |
| 4,591,499 A | 5/1986 | Linn et al. | |
| 4,689,226 A | 8/1987 | Nurmi et al. | 424/93 |
| 5,186,962 A * | 2/1993 | Hutkins et al. | 426/61 |
| 5,296,221 A | 3/1994 | Mitsuoka et al. | |
| 5,310,555 A | 5/1994 | Zimmer | |
| 5,348,881 A | 9/1994 | Vedamuthu et al. | 435/252.1 |
| 5,478,559 A | 12/1995 | Yabiki et al. | |
| 5,501,857 A | 3/1996 | Zimmer | |
| 5,547,692 A | 8/1996 | Iritani et al. | |
| 5,604,127 A | 2/1997 | Nisbet et al. | 435/252.4 |
| 5,705,152 A | 1/1998 | Plummer | |
| 5,718,894 A | 2/1998 | Mann | 424/93.3 |
| 5,725,853 A | 3/1998 | Dennis et al. | |
| 5,785,990 A * | 7/1998 | Langrehr | 424/442 |
| 5,795,602 A | 8/1998 | Craig et al. | |
| 5,849,289 A | 12/1998 | Dobrogosz et al. | |
| 5,858,356 A | 1/1999 | Wolf et al. | 424/93.45 |
| 5,876,990 A * | 3/1999 | Reddy et al. | 435/177 |
| 5,902,578 A | 5/1999 | Halpin-Dohnalek et al. | 424/93.3 |
| 5,945,333 A | 8/1999 | Rehberger | |
| 6,007,808 A | 12/1999 | De Haen et al. | |
| 6,060,050 A | 5/2000 | Brown et al. | |
| 6,090,416 A | 7/2000 | Iritani et al. | |
| 6,103,227 A | 8/2000 | Wolf et al. | 424/93.45 |
| 6,120,810 A | 9/2000 | Rehberger | |
| 6,132,710 A | 10/2000 | Panigrahi et al. | |
| 6,221,650 B1 | 4/2001 | Rehberger | |
| 6,346,422 B1 | 2/2002 | Butty et al. | |
| 6,455,063 B1 | 9/2002 | Rehberger et al. | |
| 6,461,607 B1 | 10/2002 | Farmer | |
| 6,468,525 B1 | 10/2002 | Watson et al. | 424/93.3 |
| 6,506,413 B1 | 1/2003 | Ramaekers | |
| 6,537,544 B1 | 3/2003 | Johansson et al. | |
| 6,551,708 B2 | 4/2003 | Tsuda | 428/402 |
| 7,052,688 B2 | 5/2006 | De Simone | |
| 2001/0031276 A1 | 10/2001 | Shelford et al. | 424/442 |
| 2002/0048607 A1 | 4/2002 | Muscato et al. | 424/537 |
| 2002/0187134 A1 | 12/2002 | Ranganathan | |
| 2002/0192202 A1 | 12/2002 | Naidu | 424/93.45 |
| 2003/0031659 A1 | 2/2003 | Farmer | 424/93.45 |
| 2004/0126872 A1 | 7/2004 | Rehberger | |

FOREIGN PATENT DOCUMENTS

| | | |
|---|---|---|
| CA | 2 226 501 | 1/2002 |
| EP | 0 203 586 A3 | 12/1986 |

OTHER PUBLICATIONS

Abe, F et al, "Effect of administration of bifidobacteria and lactic acid bacteria to newborn calves and piglets," (1995) J Dairy Sci 78:2838-2846.

Banach, S et al, "Influence of *Lactobacillus brevis* 1E-1 on the gastrointestinal microflora of pre-weaning and weaning pigs," (Jul. 21-25, 2002, Quebec City, Canada) Joint Meeting Abstracts, J Dairy Sci 85: Sup 1, and J Animal Sci. 80: Sup 1, p. 248.

Banach, S et al, "Influence of *Lactobacillus brevis* strain 1E-1 on the gastrointestinal microflora of pre-weaning and weaning pigs," (2002) Poster.

Barrow, P A et al, "Changes in the microflora and physiology of the anterior intestinal tract of pigs weaned at 2 days, with special reference to the pathogenesis of diarrhea," (1997) Infect and Immun 18(3):586-595.

(Continued)

*Primary Examiner*—David M. Naff
*Assistant Examiner*—Deborah K. Ware
(74) *Attorney, Agent, or Firm*—Whyte Hirschboeck Dudek S.C.

(57) ABSTRACT

A composition comprising lactic acid bacteria that are selected from at least one of *Lactococcus lactis*, *Lactobacillus lactis*, and *Lactobacillus brevis*. The composition is suitable for administration to animals. Upon administration to an animal, the composition provides at least one of the following (a) improves performance in the animal and (b) reduces scours in animals. Also provided is a method of treating an animal in which the composition is administered to the animal. A method of forming a direct-fed microbial is also provided. A culture including the lactic acid bacteria is grown in a liquid nutrient broth. The lactic acid bacteria are separated from the liquid nutrient broth. The lactic acid bacteria can be freeze dried.

17 Claims, 7 Drawing Sheets

OTHER PUBLICATIONS

Bechman, T J et al, "Influence of *Lactobacillus acidophilus* on performance of young dairy calves," (1977) J Dairy Science Supp 60, p. 74. (Abstract).

Benoit, V et al, "Characterization of Brevicin 27, a bacteriocin synthesized by *Lactobacillus brevis* SB27," (1994), Current Microbiol, 28(1):53-61.

Brown, D C et al, "Effect of milk supplementation with *Lactobacillus brevis* 1E-1 on intestinal microflora, intestinal morphology and pig performance," (2003) J Animal Sci v 81: Supp 2, p. 76 (Abstract).

Christen, S D et al, "The effect of direct-fed microbials on the performance of pre-weaned Holstein calves," (1995) J Animal Science v 73 (Supp 1):249 (Abstract).

Coventry, M J, "Production of Brevicin 286 by *Lactobacillus brevis* VB286 and partial characterization," (1996) J Applied Bacteriology, 80, 91-98.

Cruywagen, C W et al, "Effect of *Lactobacillus acidophilus* supplementation of milk replacer on preweaning performance of calves," (1996) J Dairy Sci 79:483-486.

Davis, M E et al, "Influence of *Lactobacillus brevis* 1E-1 on the gastrointestinal microflora, gut morphology, and pig performance pre- and post-weaning," 9th Intl Sym Digestive Physiology in Pigs, Banff, AB, Canada (2003) 2:265-267.

Galbraith, E A et al, "Characterization of the predominant lactic acid bacteria isolated from the intestinal tract of the pre-weaned calves," Abstracts Am Soc Microbiol 102d General Meeting, Salt Lake City, UT (May 19-23, 2002) (Abstract #Z-14).

Galbraith, E A et al, Characterization of predominant lactic acid bacteria isolated from the intestinal tract of the pre-weaned calves (May 2002) (Poster).

Jenny, B. F. et al, "Performance and fecal flora of calves fed a *Bacillus subtilis* concentrate," (1991) J Dairy Sci 74:1968-1973.

Jin, L. Z. et al, "Growth performance, intestinal microbial populations, and serum cholesterol of broilers fed diets containing *Lactobacillus cultures*," (1998) Poultry Sci 77:1259-1265.

Krause, Denis O et al, "Ribotyping of adherent Lactobacillus from weaning pigs: a basis for probiotic selection based on diet and gut compartment," (1997) Anaerobe 3:317-325.

Lewus, Catherine B et al, "Detection of bacteriocins produced by lactic acid bacteria," (1991) J Microb Methods 13:145-150.

Morrill, J L et al, "Plasma proteins and a probiotic as ingredients in milk replacer," (1995) J Dairy Sci 78:902-907.

O'Brien, M L et al, "Effect of feeding a novel direct fed microbial in a calf milk replacer," (2003) J Anim Sci v 81, Supp 1/ J Dairy Sci, v 86, Supp 1, p. 22 (Abstract).

Odle, J et al, "Nutritional approaches for improving neonatal piglet performance: liquid diets for early-weaned pigs," (1998) Proc 8th World Conf Animal Produc, Seoul, KR, v 8, p. 35-44.

Parrott, T D et al, "Characterization of the predominant Lactobacilli isolated from the gastrointestinal tract of post-weaned pigs," 95th Gen'l Meeting Am Soc Microbio, May 23-27, 1994, Las Vegas, NV, p. 255 (Abstract).

Rehberger, T G, "Genome analysis of Propionibacterium freudenreichii by pulsed-field gel electrophoresis," (1993) Curr Microbiol 27:21-25.

Ruppert, L D et al, "Feeding of probiotics to calves," (1994) J Anim Sci v 72, Supp 1/J Dairy Sci v 77, Supp 1, p. 296 (Abstract).

Sambrook et al, "Molecular cloning: A laboratory manual," 3d Ed. (2001) Cold Spring Harbor Lab Press, N Y (ref book-copy not provided).

Savage, D C, "The ecological digestive system and its colonisation," (1989) Revue Sci Tech Off Int Epiz 8 (2):259-273.

Savage, D C, "Factors influencing biocontrol of bacterial pathogens in the intestine," (1987) Food Techno 41:82-87.

Schutz, H and Radler, F, "Anaerobic reduction of glycerol to propanediol-1.3 by *Lactobacillus brevis* and *Lactobacillus buchneri*," (1984) Sys Appl Microbiol, 5:169-178.

Schwab, C G et al, Performance and fecal flora of calves fed nonviable *Lactobacillus bulgaricus* fermentation product, (1980) J Dairy Sci, 63:1412-1423.

Specian, R D and Oliver, M G, "Functional biology of intestinal goblet cells," (1991) Am J Physiol, 260 (Cell Physiol 29):C183-C193.

Tannock, G W et al, "Lactobacillus succession in the piglet digestive tract demonstrated by plasmid profiling," (May 1990), Applied and Environmental Microbio 56(5), pp. 1310-1316.

Tannock, G W et al, "Identification of Lactobacillus isolates from the gastrointestinal tract, silage, and yoghurt by 16S-23S rRNA gene intergenic spacer region sequence comparison," (1999) 65(9) pp. 4264-4267.

Tilsala-Timisjarvi, A and Talatossava, T, "Development of ogligonucleotide primers from the 16S-23S rRNA intergenic sequences for identifying different dairy and probiotic lactic acid bacteria by PCR," (1997) Int J Food Microbiol 35:49-56.

Tomkins, T J et al, "Milk replacer research leads to new developments," (1994) Feedstuffs 66(42):13-23.

USDA Appendix B (2002): Overall reproductive efficiency and health statistics of U. S. animal agriculture (6 pages).

Vanhorn, H H et al, "Large dairy herd management," (1992) Am Dairy Sci Assoc, Champaign, IL. (ref book-copy not provided).

* cited by examiner

Figure 1: Populations of lactobacilli isolated from the digestive tracts of calves
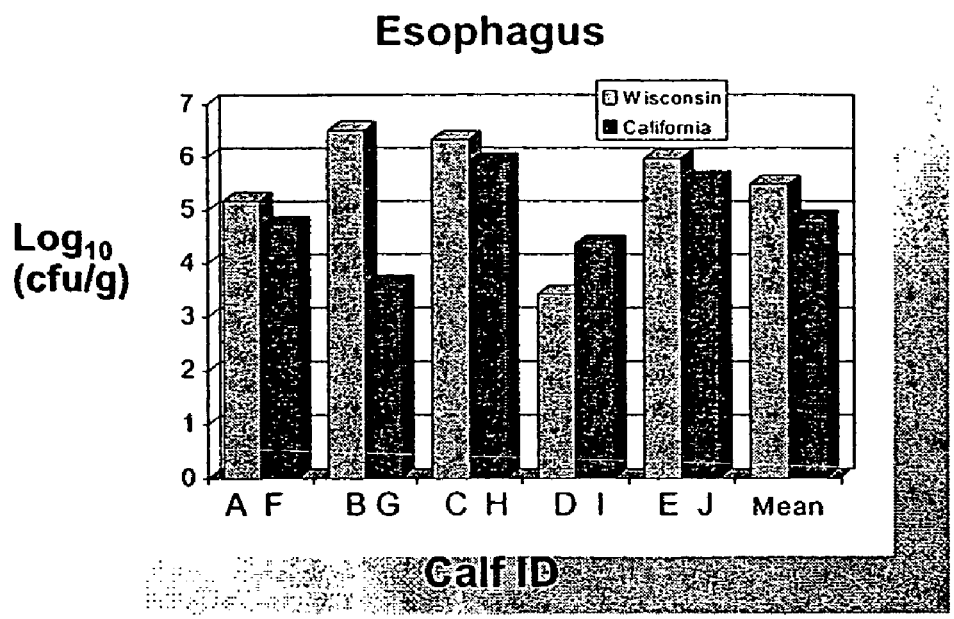
Figure 2: Populations of lactobacilli isolated from the digestive tracts of calves
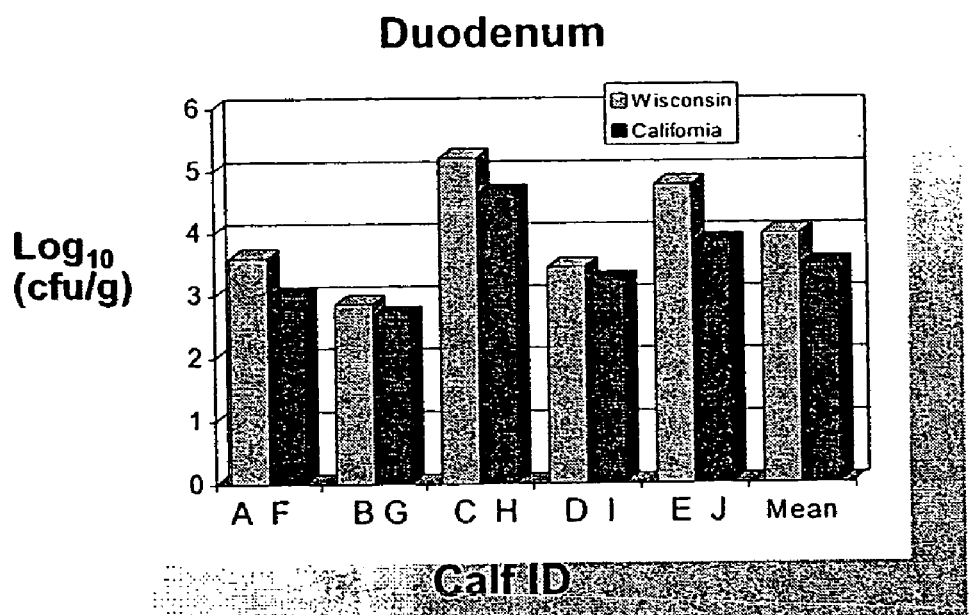

Figure 3: Populations of lactobacilli isolated from the digestive tracts of calves
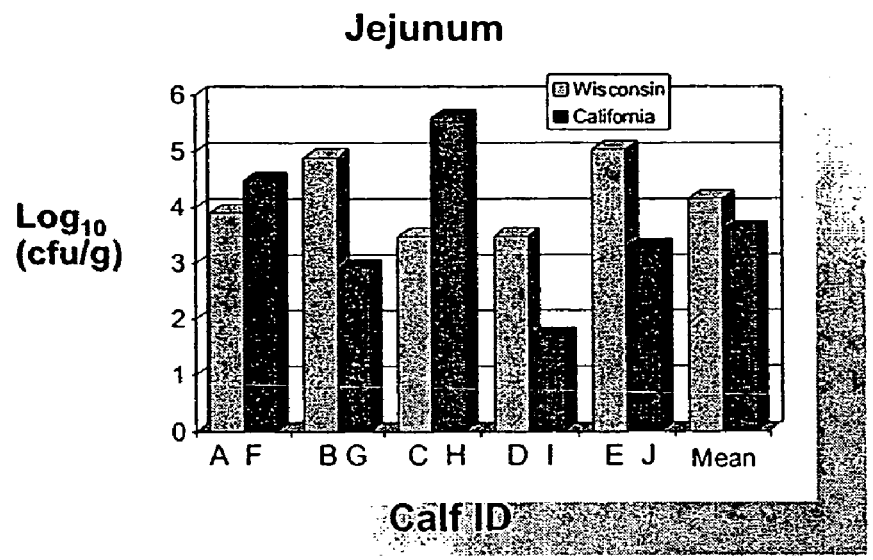
Figure 4: Populations of lactobacilli isolated from the digestive tracts of calves
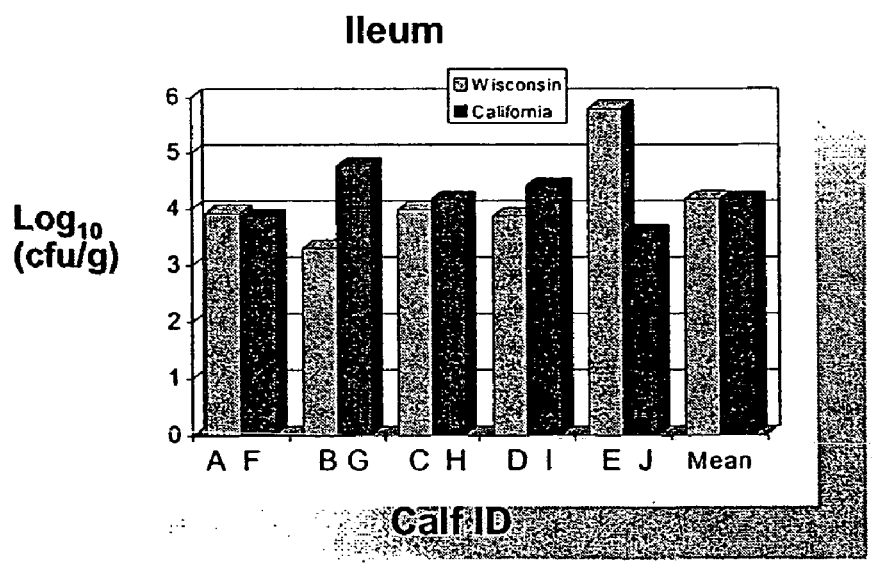

Figure 5: Populations of lactobacilli isolated from the digestive tracts of calves
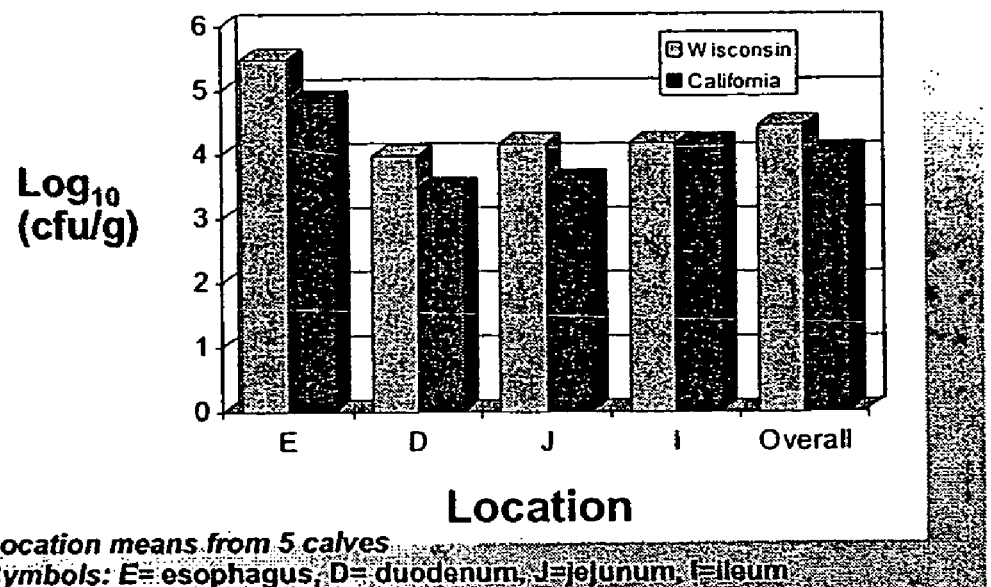
Location means from 5 calves
Symbols: E= esophagus, D= duodenum, J=jejunum, I=ileum
Figure 6: Lactic acid isolates producing antagonistic activity against prominent pathogens
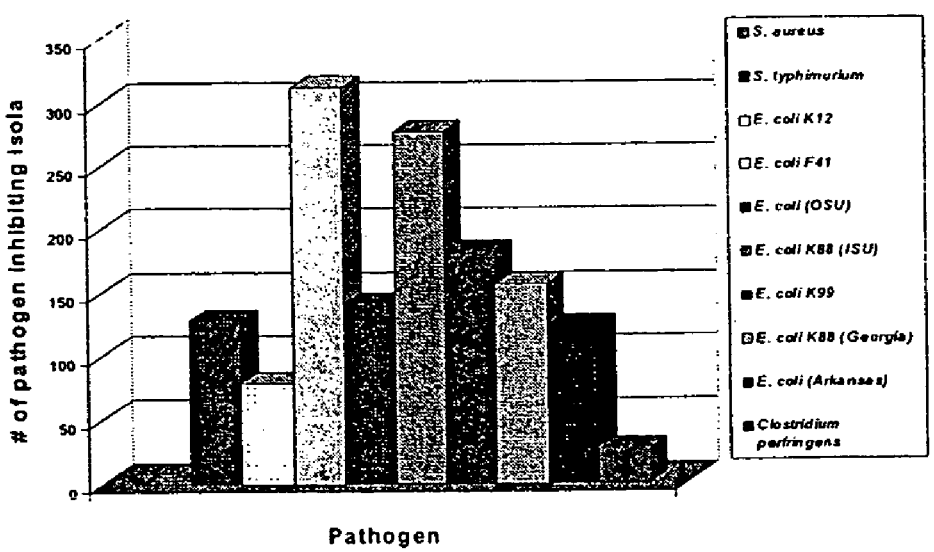

*Figure 7: Lactic acid isolates producing antagonistic activity against prominent pathogens*
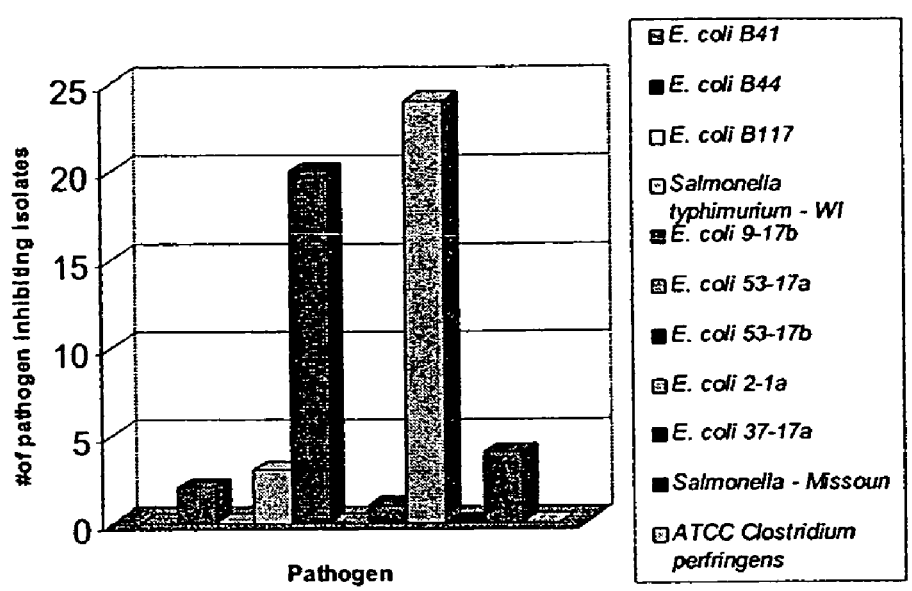

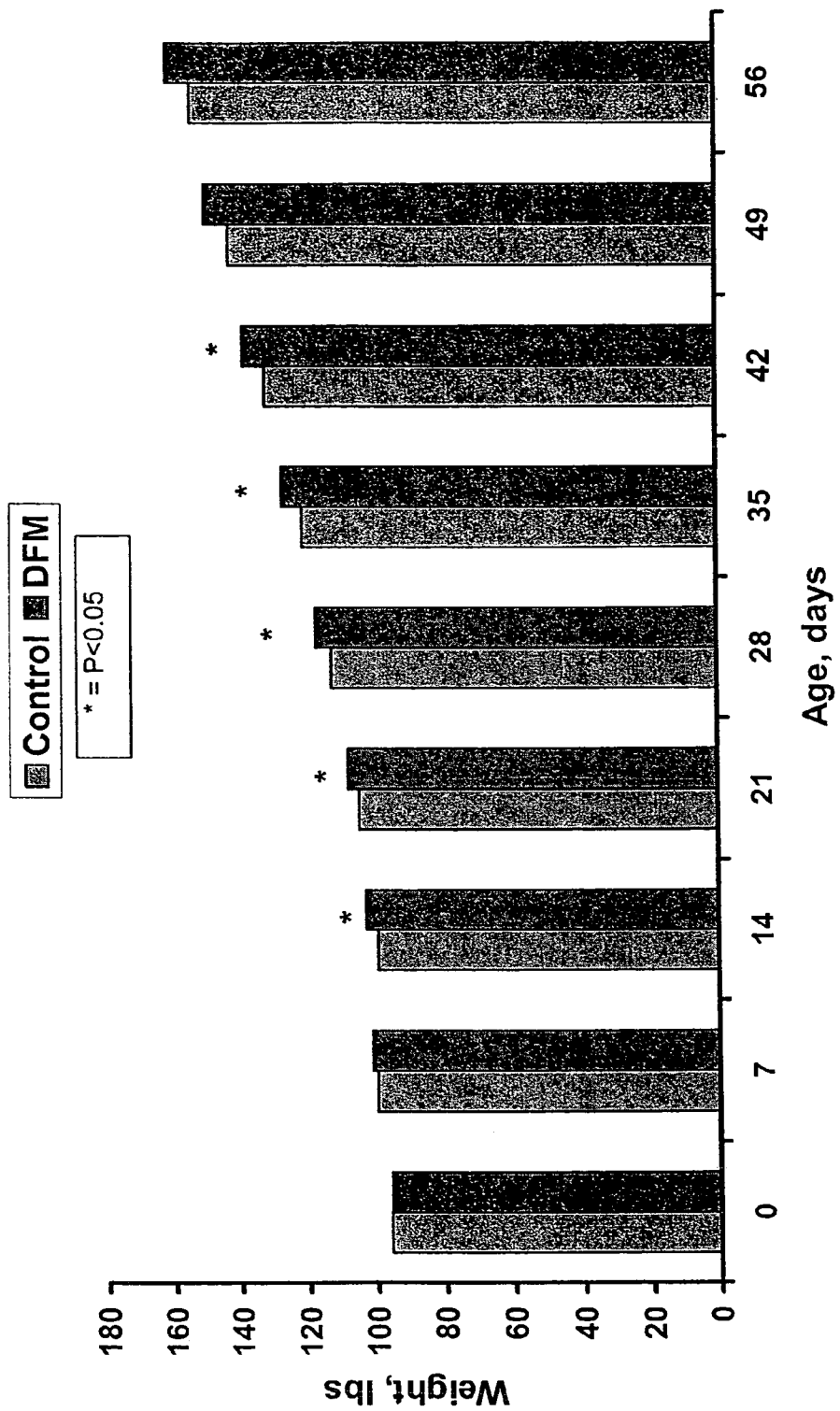

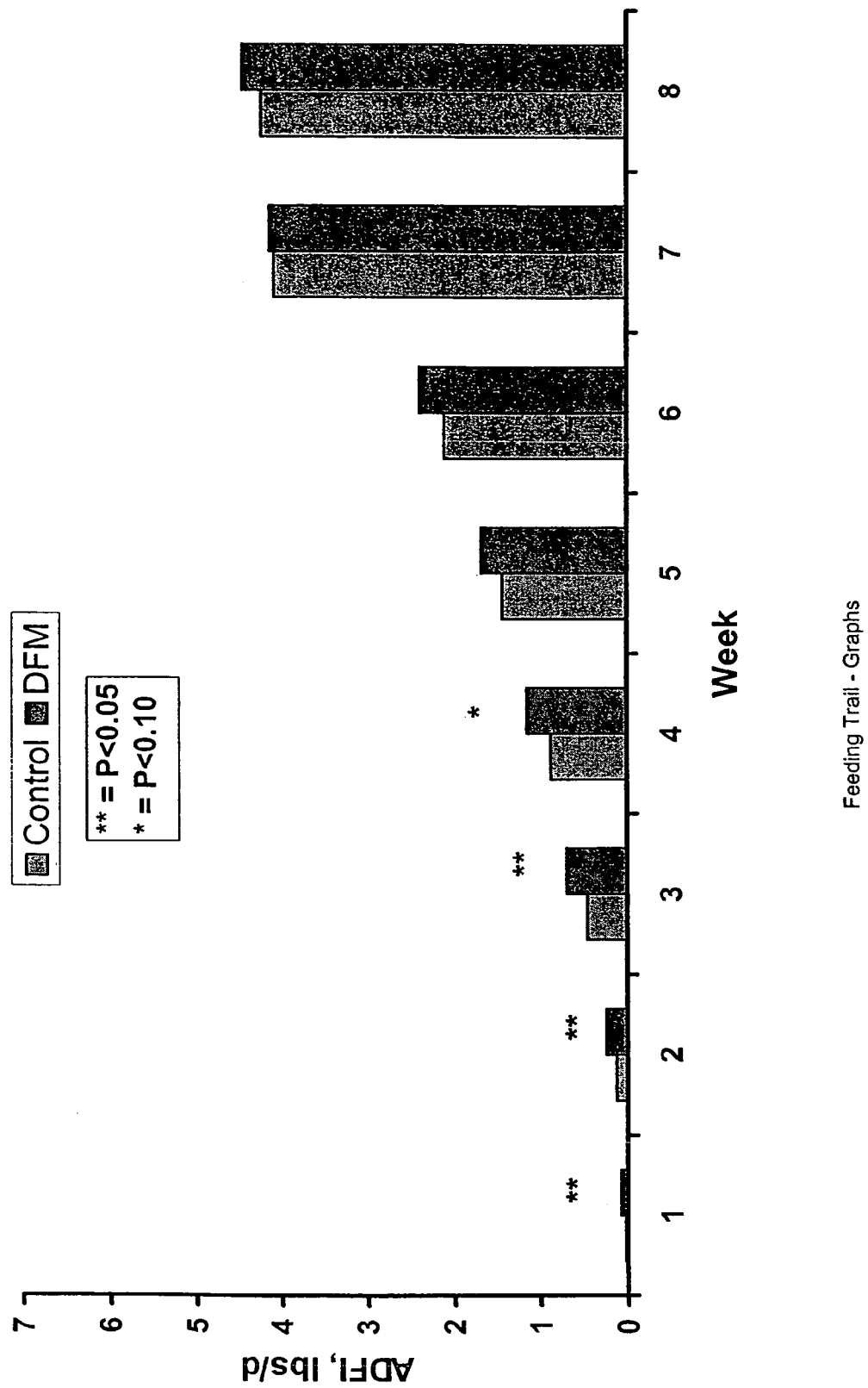

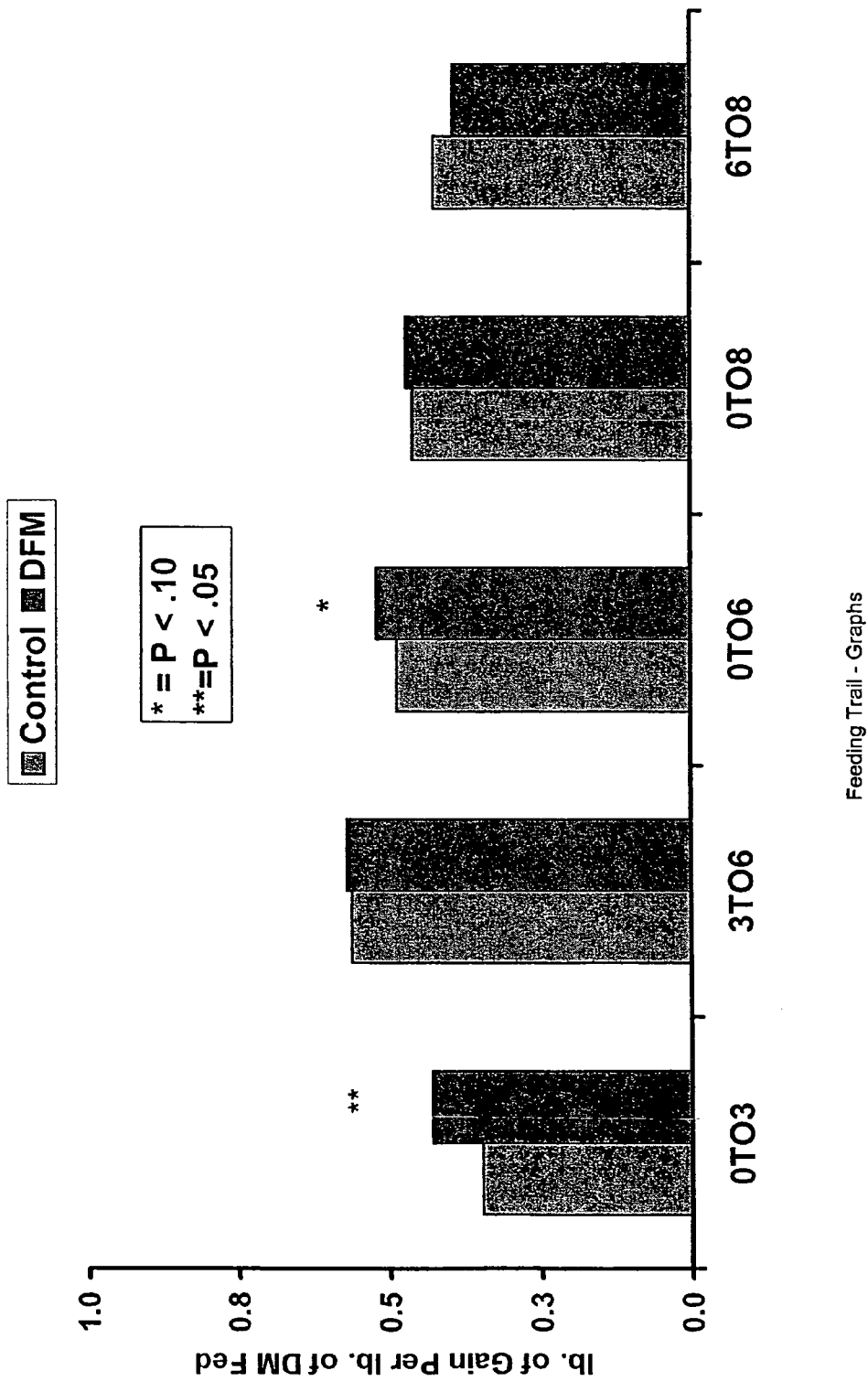

LACTIC ACID BACTERIA AND ITS USE IN DIRECT-FED MICROBIALS

CROSS REFERENCE TO RELATED APPLICATION

This application claims the benefit of U.S. Provisional Patent Application No. 60/480,663, filed on Jun. 23, 2003, that is entitled Lactic Acid Bacteria for Use in Direct-Fed Microbials, the entire disclosure of which is incorporated herein by reference.

BIBLIOGRAPHY

Complete bibliographic citations of the references referred to herein by the first author's last name in parentheses can be found in the Bibliography section, immediately preceding the claims.

FIELD OF THE INVENTION

The invention relates to lactic acid bacteria. More particularly, though not exclusively, the present invention relates to lactic acid bacteria that are useful as a direct-fed microbial for animals, such as calves.

DESCRIPTION OF THE RELATED ART

In 2002, the National Animal Health Monitoring System (NAHMS) published a Dairy 2002 study that stated that over 8.7% of dairy replacement calves born alive die prior to weaning. Of the 8.7% of dairy replacement calves that died, 62.1% of them died from scours, i.e., diarrhea, or other digestive disorders (USDA, 2002).

Scours increases during stress. Maintenance of a healthy intestine microflora in a calf is extremely important during stress, since stress is known to increase the turn over rate of the intestinal microflora. Stress is induced by a number of environmental factors common in production livestock operations such as dietary changes, weaning, shipping, weather, handling and crowding. During these times, opportunistic pathogenic organisms that are present in the animal's environment can establish in the intestinal tract and initiate an infection. A common symptom of this infection is scours or diarrhea. Maintenance of a normal healthy intestine microflora has been shown to prevent the colonization of the intestinal tract with these opportunistic pathogens.

Unique compositions of microflora in the intestinal tract are essential to maintain the functional integrity and health of a host organism. The presence of lactic acid bacteria in the intestinal tract of dairy calves is well documented and may provide an advantage to the host animal. However, the distribution and diversity of lactic acid bacteria in the intestinal tract of pre-weaned calves is not well known.

Performance of a calf includes average daily weight gain, overall weight gain, and feed efficiency. Feed efficiency is the ratio of feed consumed by an animal versus the pounds gained by the animal. Performance can be related to scours, since intake diverted to scours can take away from intake that increases performance. Current industry practices to increase performance in pre-weaned calves generally include feeding antibiotics or ionophores at subtherapeutic levels. Antibiotics, such as neomycin or oxytetracycline, influence performance of dairy replacement calves through increasing growth and feed efficiencies (Tomkins et al., 1994). However, the practice of feeding antibiotics to livestock has raised concerns about increasing the antibiotic resistance of microbial pathogens in the food supply.

Ionophores are feed additives that influence volatile fatty acid and methane production in the rumen to favor growth and feed efficiency. Coccidiostats are agents that are useful in the treatment or prevention of coccidiosis. Some coccidiostats, such as lasalocid, also influence the growth performance of the calf by acting as an ionophore (Van Horn and Wilcox, 1992). Nevertheless, the use of ionophores is limited to use in pre-weaned calves. Furthermore, widespread use of coccidiostats in animal feed raises concerns about the nurturing of drug resistance among populations of microorganisms.

One approach to improving the health of animals is to alter the inhabitants of their gastrointestinal tract. Altering the inhabitants of the gastrointestinal tract of animals has been attempted by feeding direct-fed microbials to animals. The efficacy of single or multiple strains of bacteria commonly used in commercial direct-fed microbials has been and continues to be debated. This debate is primarily due to inconsistent performance of previous direct-fed microbials. This inconsistency may be due to the fact that many commercial direct-fed microbials are composed of lactic acid bacteria strains commonly used as silage inoculants or cheese starter cultures. These strains may be effective to inoculate silage or to convert milk into cheese but have no proven efficacy as direct fed microbials for animal feeding. While the "one strain for all products" approach may be an economical method for the commercial fermentation industry, this does not provide the best strains for each application.

SUMMARY OF THE INVENTION

The invention is intended to solve at least some of the problems noted above. A composition is provided and includes lactic acid bacteria that are chosen from at least one of *Lactococcus lactis, Lactobacillus lactis*, and *Lactobacillus brevis*. The composition is suitable for administration to animals. Upon administration to an animal, the composition, the composition provides at least one of the following (a) improves performance in the animal and (b) reduces scours in the animal.

A method of treating an animal is also provided. In the method, the above-described composition is administered to an animal. In one embodiment, the composition is fed to dairy replacement calves. By improving the intestinal health of dairy replacement calves, it is possible to decrease not only the percentage of calves that die due to digestive problems, but also the overall mortality and morbidity of these animals.

Also provided is a method of forming a direct-fed microbial. In the method, a culture is grown in a liquid nutrient broth. The culture includes lactic acid bacteria that are chosen from at least one of *Lactococcus lactis, Lactobacillus lactis*, and *Lactobacillus brevis*. The lactic acid bacteria are suitable for administration to animals. Upon administration to an animal, the lactic acid bacteria provide at least one of the following (1) improves performance in the animal and (2) reduces scours in the animal. The lactic acid bacteria are separated from the liquid nutrient broth.

BRIEF DESCRIPTION OF THE DRAWINGS

Preferred exemplary embodiments of the invention are illustrated in the accompanying drawings.

FIG. 1 is a graph showing populations of lactic acid bacteria isolated from the esophagus of calves from Wisconsin and California.

FIG. 2 is a graph showing populations of lactic acid bacteria isolated from the duodenum of calves from Wisconsin and California.

FIG. 3 is a graph showing populations of lactic acid bacteria isolated from the jejunum of calves from Wisconsin and California.

FIG. 4 is a graph showing populations of lactic acid bacteria isolated from the ileum of calves from Wisconsin and California.

FIG. 5 is a graph showing populations of lactic acid bacteria isolated from the digestive tracts of calves from Wisconsin and California.

FIG. 6 is a graph showing the number of lactic acid isolates inhibiting general pathogen growth ranged from zero (*Staphylococcus aureus*) to 312 (*Escherichia coli* F41).

FIG. 7 is a graph showing the antagonistic activity of lactic acid isolates against one strain of *E. coli* (B44) from Barron, Wis. (two isolates), *E. coli* from Missouri (one isolate), and *Salmonella typhimurium* from both Wisconsin (three isolates) and Missouri (four isolates).

FIG. 8 is a graph showing the effect of a direct-fed microbial made in accordance with the invention and including six most preferred lactic acid bacteria strains on weight gain in calves.

FIG. 9 is a graph showing the effect of the direct-fed microbial of FIG. 8 on feed intake in calves.

FIG. 10 is a graph showing the effect of the direct-fed microbial of FIG. 8 on feed efficiencies in calves.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

In accordance with the present invention, there may be employed conventional molecular biology and microbiology within the skill of the art. Such techniques are explained fully in the literature. See, e.g., Sambrook, Fritsch & Maniatis, Molecular Cloning: A Laboratory Manual, Third Edition (2001) Cold Spring Harbor Laboratory Press, Cold Spring Harbor, N.Y.

Lactic acid bacteria of the invention can be isolated from animals, such as from cows, cattle, sheep, pigs, deer, goats, elk, and other animals. In a preferred embodiment, lactic acid bacteria are isolated from calves.

In the Examples below, the lactic acid bacteria were isolated from the gastrointestinal tract of pre-weaned calves. Specifically, the lactic acid bacteria were isolated from the esophagus, jejunum, duodenum, and ileum of healthy calves. However, suitable lactic acid bacteria taken from any portion of the gastrointestinal tract of the animal can be used within the scope of the present invention.

The lactic acid bacteria were screened for antagonistic activity against prominent pathogenic microorganisms isolated from calves. Several non-limiting strains of the lactic acid bacteria were identified. The lactic acid bacteria were then tested in animals to determine whether the lactic acid bacteria improved various health parameters of the animals. Animals that can be fed the bacteria include, but are not limited to, cows, cattle, calves, sheep, pigs, deer, goats, and elk.

The ability of the selected lactic acid bacteria to improve the health and performance of calves was evaluated. When fed to calves, the lactic acid bacteria strains, fed as a direct-fed microbial, reduced scours in some groups of calves and improved performance in some groups of calves. An improvement in performance, as used herein, means an improvement in at least one of average daily weight gain, weekly weight gain, total weight gain, conversion, which includes both feed:gain and gain:feed, feed efficiency, percent calves weaned, and feed intake. In a first preferred embodiment, after about 42 days of feeding the direct-fed microbial to a calf having a decreased initial health status, performance is improved by at least about 15%, and more preferably at least about 25%. In another preferred embodiment, after about 42 days of feeding the direct-fed microbial, scours in the calf are reduced by at least about 15%, and more preferably by at least about 25%, and even more preferably by at least about 50%.

Characterization and Screening of Lactic Acid Bacteria:

In one exemplary evaluation of the bacteria of the present invention, the predominant lactic acid bacteria found in the intestinal tract of pre-weaned calves from Wisconsin and California dairy farms were characterized. The intestinal tracts from five pre-weaned calves raised in Wisconsin and five pre-weaned calves raised in California were sampled. The greatest numbers of lactic acid bacteria across intestinal samples from all calves were found in esophageal samples ($7.8 \times 10^5$ CFU/g), while duodenal samples yielded the fewest lactic acid bacteria ($2.8 \times 10^4$ CFU/g). Twenty-five numerically dominant isolates were selected from segments of the esophagus, duodenum, jejunum, and ileum of each calf.

Genomic DNA from each isolate was screened using random amplified polymorphic DNA polymerase chain reaction (RAPD-PCR) analysis with two primers, and the prevalence and genetic similarity of strains were identified using cluster analysis. Thirty-nine major clusters emerged at a similarity of 10%. Of 1000 isolates examined by RAPD-PCR analysis with both primers, 485 isolates were found to be identical to at least one other isolate. However, 136 of the isolates were identical to only one other isolate. Though fairly heterogeneous populations of lactic acid bacteria were found in both Wisconsin and California calves, genotypes common to both states were present in four of the thirty-nine clusters of strains.

The numerically predominant strains were also identified biochemically. The biochemical identification of numerically predominant strains from Wisconsin and California supported the heterogeneity found by RAPD-PCR analysis. The results indicate a diverse population of lactic acid bacteria exists within the intestinal tract of healthy, pre-weaned calves.

Representative strains from each of the thirty-nine major clusters were screened for antagonistic activity against known pathogens. Based on this screening of the numerically predominant strains, a number of preferred lactic acid bacteria strains were identified. These strains showed useful properties when used individually or in combination. Preferred strains include strains of the genus *Lactococcus* and *Lactobacillus*, although many other strains of lactic acid bacteria are also effective and can be used in the invention. Even more preferred strains are strains that are *Lactococcus lactis* (formerly known as *Streptococcus lactis*), *Lactobacillus lactis*, and *Lactobacillus brevis*. The antagonistic activity screening identified six most preferred and particularly useful, although not limiting, strains: AJ25, HE17, JD19, CI15, DJ6, and ID7.

Direct Feed Assays on Calves:

Studies were done to determine the effect of feeding a direct-fed microbial containing the six most preferred strains, i.e., AJ25, HE17, JD19, CI15, DJ6, and ID7. The direct-fed microbial was fed in a calf milk replacer. Holstein bull calves (n=120), less than 7 d of age were purchased from an area sale barn in two groups of 60 calves. Two experiments (Experiments 1 and 2) were conducted using a randomized complete block design. The details of Experiments 1 and 2 are discussed below in the Examples Section.

Strains AJ25, HE17, JD19, CI15, DJ6, and ID7 are available from the microorganism collection of the American Type Culture Collection, 10801 University Blvd., Manassas, Va. 20110, under accession numbers as follows: *Lactobacillus brevis* AJ25 (PTA-6099), *Lactobacillus brevis* HE17 (PTA-6100), *Lactococcus lactis* JD19 (PTA-6104), *Lactobacillus lactis* CI15 (PTA-6101), *Lactobacillus lactis* DJ6 (PTA-6102), and *Lactococcus lactis* ID7 (PTA-6103). All strains were deposited on Jun. 22, 2004.

Calves were assigned by weight to a control (CON) diet or a diet containing the direct-fed microbial (DFM). All calves were fed a milk replacer formulated to contain protein and fat levels at 20% of dry matter (DM) and were fed 454 g/d. Calves were housed in individual hutches with water available ad libitum from d 0. A commercial calf starter was available free choice ad libitum beginning at d 1. Feed intake, scour scores, and antibiotic treatments were recorded daily. Calves were weighed weekly. Calves were weaned at d 42 dependent on a minimum intake of 454 g of calf starter for 3 consecutive days.

Experimental data were analyzed separately due to treatment by trial interactions. Initial serum immunoglobulin G (IgG) level for calves in Experiment 1 was 50% lower than for calves in Experiment 2 (3.9 vs. 7.9 mg/ml, P<0.10). Calves fed the DFM diet in Experiment 1 were significantly heavier than calves fed the CON diet beginning on d 14 and maintained the difference through d 42. Average daily gains (ADG) were significantly greater for the first six weeks of the study for calves fed the DFM diet compared to those fed the CON diet (465 g vs. 393 g respectively). In Experiment 1, calves fed the DFM diet had a lower percent scouring than calves fed the CON diet (28% vs. 39%, respectively, P=0.35).

In Experiment 2, there was no significant difference in average weekly weight gains, average daily gain (ADG), average daily feed intake, or gain:feed between calves fed the DFM or CON diet. However, for calves fed the DFM diet, the percentage of calves that scoured was significantly (P=0.05) less than calves fed the CON diet (18% vs. 41%, respectively). These results show that the direct-fed microbial utilized in this study is beneficial for the reduction in percentage of calves scouring and improves calf performance.

Preparation and Feeding Direct-Fed Microbials:

A direct-fed microbial of the invention includes lactic acid bacteria. The lactic acid bacteria may be presented in various physical forms, for example, as a top dress, as a water soluble concentrate for use as a liquid drench or to be added to a milk replacer, gelatin capsule, or gels. In a preferred embodiment of the top dress form of the lactic acid bacteria, freeze-dried lactic acid bacteria fermentation product is added to a carrier, such as whey, maltodextrin, sucrose, dextrose, limestone (calcium carbonate), rice hulls, yeast culture, dried starch, sodium silico aluminate. In a preferred embodiment of the water soluble concentrate for a liquid drench or milk replacer supplement, freeze-dried lactic acid bacteria fermentation product is added to a water soluble carrier, such as whey, maltodextrin, sucrose, dextrose, dried starch, sodium silico aluminate, and a liquid is added to form the drench or the supplement is added to milk or a milk replacer. In a preferred embodiment of the gelatin capsule form, freeze-dried lactic acid bacteria fermentation product is added to a carrier, such as whey, maltodextrin, sugar, limestone (calcium carbonate), rice hulls, yeast culture dried starch, and/or sodium silico aluminate. In a preferred embodiment, the lactic acid bacteria and carrier are enclosed in a degradable gelatin capsule. In a preferred embodiment of the gels form, freeze-dried lactic acid fermentation product is added to a carrier, such as vegetable oil, sucrose, silicon dioxide, polysorbate 80, propylene glycol, butylated hydroxyanisole, citric acid, ethoxyquin, and artificial coloring to form the gel.

Lactic acid bacteria are fed to an animal. When fed to a calf, the lactic acid bacteria become established in its gastrointestinal tract. Preferably, the amount of the lactic acid bacteria that is delivered to the animal is about $1 \times 10^9$ CFU/animal/day to about $5 \times 10^{10}$ CFU/animal/day. In a more preferred embodiment, about $5 \times 10^9$ CFU/animal/day to about $1 \times 10^{10}$ CFU/animal/day of the lactic acid bacteria is delivered to the animal. In one preferred embodiment, lactic acid bacteria in any of the above preferred physical forms are directly fed to a calf to improve performance and/or decrease scours.

To obtain the lactic acid bacteria and to form the direct-fed microbial, the lactic acid bacteria are preferably fermented to between about a $1 \times 10^9$ CFU/ml level to about a $1 \times 10^{10}$ CFU/ml level, with a level of about $2 \times 10^9$ CFU/ml being more preferred. The bacteria are harvested by centrifugation, and the supernatant is removed. The pelleted lactic acid bacteria can then be fed to the calf. Preferably, the pelleted lactic acid bacteria are freeze-dried for direct feeding to the calf.

In a preferred embodiment, lactic acid bacteria are added to animal feed. More preferably, lactic acid bacteria are fed as a mixture of freeze-dried lactic acid bacteria, which is at a concentration of about $6.5 \times 10^9$ CFU/g, and a carrier, which preferably is a maltodextrin carrier although other carriers can also be used. The lactic acid bacteria are preferably fed from about birth to about 6 weeks of age, although the lactic acid bacteria can be fed for different durations and at different times.

EXAMPLES

The following Examples are provided for illustrative purposes only. The Examples are included herein solely to aid in a more complete understanding of the presently described invention. The Examples do not limit the scope of the invention described or claimed herein in any fashion.

Example 1

Isolation of Lactic Acid Bacteria

A. Materials and Methods

1. Calf Selection and Intestinal Extraction Procedures:

A total of ten healthy, pre-weaned calves (approximately 80 lbs each) were purchased from separate sale barns in Wisconsin (five calves) and California (five calves). Calves were killed by exsanguation and samples of the esophagus, duodenum, jejunum, and ileum were aseptically removed along with 25 g samples of fecal and stomach contents from each calf. The intestinal, fecal, and stomach samples were transported to Agtech Products Inc., for dissection and culture isolation.

2. Isolation and Culture Maintenance Procedures:

Esophageal, duodenal, jejunal, and ileal sections were washed with 100 ml of sterile buffer (0.3 mM $KH_2PO_4$, 1 mM $MgSO_4$, 0.05% cysteine hydrochloride, pH 7.0), and cut open with surgical scissors to expose the epithelial lining. To remove lactic acid bacterial cells from intestinal tissue, 22 g samples of the intestinal tissue were placed in sterile bags and agitated in a stomacher for 60 sec. Stomach and fecal contents were also suspended in sterile buffer and mixed by stomaching. Lactic acid bacterial populations were enumerated on LBS agar (Becton Dickinson, Sparks, Md.) incubated anaerobically (Pack-Anaero, Mitsubishi Gas Chemical, New York) for 48 h at 37° C. Twenty-five isolated colonies from the highest dilution of each tissue sample were picked into 10 ml tubes of MRS broth. The strains were stored in MRS broth (available from PlantMedia, Dublin, Ohio and Thomas Scientific, Swedesboro, N.J.) containing 10% glycerol at −80° C. and routinely propagated in MRS broth at 37° C.

3. Biochemical and Genetic Identification Procedures:

Random amplified polymorphic DNA polymerase chain reaction (RAPD-PCR) analysis was used as a DNA fingerprinting method to identify strains. Additionally, standard biochemical identification procedures were performed using the BIOLOG MicroLog 2 system (BIOLOG, Hayward, Calif.) to identify the species names of select isolates.

a. DNA Isolation:

A 1% inoculum taken from a 24-hour culture was placed into 10 ml of sterile MRS broth and incubated at 37° C. until the optical density (660 nm) reached 0.8-1.0 (log phase). Cell suspensions were then harvested by centrifugation (2800 rpm for 8 min). The supernatant was decanted and the pellet resuspended in the appropriate amount of Tris-EDTA buffer containing 15% sucrose to obtain a concentration of $2 \times 10^9$ CFU/ml. Genomic DNA was isolated from the lactic acid strains using a commercial genomic DNA isolation kit according to the manufacturer's instructions (Roche Diagnostics Corporation, Indianapolis, Ind.). The eluted DNA was stored at −20° C. until RAPD-PCR analysis.

b. Primers and PCR Conditions:

For RAPD-PCR analysis, PCR amplifications were carried out in 25 μl volumes. RAPD-PCR analysis was performed using Ready-to-Go RAPD-PCR Beads (Amersham Biosciences, Piscataway, N.J.) which contain two thermostable polymerases (AmpliTAQ and the Stoffel fragment), dNTPs and buffer in a room temperature stable bead. 5 μl of primer (5 pmol/μl), 4 μl of the genomic DNA (about 250 ng), and 16 μl of $dH_2O$ were added to each bead, the contents mixed and loaded into the thermal cycler. Amplification for all RAPD-PCR analysis was performed in a thermal cycler (Perkin-Elmer, Foster City, Calif.) programmed for one cycle of 4 minutes at 95° C. followed by 45 cycles at 94° C. for 1 minute, 36° C. for 1 minute, and 72° C. for 2 minutes. Two ten-base oligonucleotide primers were commercially purchased and tested for use in this reaction. Amplified DNA fragments were then separated by gel electrophoresis using a 1.0% gel at 80-100 volts.

c. Genotype Analysis:

Following ethidium bromide staining, DNA fragments were visualized and gel images were captured using Syngene's Genesnap darkroom system (Frederick, Md.). Bionumerics software (Kortrigjk, Belgium) was used for molecular weight determination of DNA fragments, cluster analysis, and dendrogram formation.

B. Results and Discussion

1. Enumeration Results

Predominant lactic acid bacteria were successfully isolated from esophageal, duodenal, jejunal, and ileal samples of both Wisconsin and California calves. The quantity of lactic acid bacteria found in each intestinal segment differed between the two groups of calves. Wisconsin calves showed higher numbers of lactic acid bacteria in the esophagus, duodenum, and jejunum (FIGS. 1, 2, 3, respectively). However, the Wisconsin and California calves contained an equal number of lactic acid bacteria in the ileum (FIG. 4). These differences may be due primarily to calf age at the time of intestinal sampling. Because the California calves were a few days younger than the Wisconsin calves, the colonization of their intestinal tract may not have been as complete as that of the older Wisconsin animals. The esophagus had the highest numbers of lactic acid bacteria among all segments that were examined (FIG. 5). This may be due to the natural exposure of the esophagus to a broader environment of bacteria than might be encountered by the more internal duodenum or jejunum.

2. Genomic Profile Results

Genomic profiles were identified for all Wisconsin (500) and California (476) calf isolates by RAPD-PCR analysis with two different primers. Isolates showing identical banding patterns for both primers were considered to be genetically identical. DNA fragment pattern analysis grouped the isolates into 39 genetically different clusters. The nodes on the dendrogram represent completely identical (100% similar) isolates. A 10% similarity cut-off was used to compare strains, classifying isolates into unique genotypic clusters. Despite the apparent genetic diversity, large clusters containing the most frequently observed genotypes were identified for both Wisconsin and California isolates. For instance, the most prevalent Wisconsin genotype was representative of 7.4% of all Wisconsin isolates. Additionally, cluster analysis yielded two especially common genotypes among California isolates. These widespread genotypes were each representative of about 10% of the California isolates. In conjunction with the examination of predominant genotypes exclusive to either Wisconsin or California calves, genotypes common to both groups of calves were studied. Four genotypic clusters contained isolates that were common to both groups of calves.

Several patterns became evident during analysis of the strains. Six of the 39 clusters contained isolates that were nearly exclusive to an individual calf. This indicates homogeneity of the lactic acid bacteria within the gastrointestinal tract of an individual animal. Furthermore, clustering of strains common to a particular intestinal segment was also observed. This depicts a relationship between the prevalence of a strain and the particular intestinal region of a calf. For example, the largest genotypic group of Wisconsin isolates contained strains strictly found in the jejunal region, but common to calves B, D, and E.

The digital documentation data from all isolates, along with biochemical analyses allowed for identification of the most predominant lactic acid bacteria from both Wisconsin and California calves. The results indicate a diverse population of lactic acid bacteria exists within the intestinal tract of healthy pre-weaned calves.

Example 2

Antimicrobial Spot Assay Procedures

A. Materials and Methods

Spent broth from a 24-hour culture of each isolate was spotted onto Tryptic Soy Agar (TSA) plates inoculated at 1% with a selected pathogen. Pathogens were prepared by growth at 37° C. in Tryptic Soy Broth to an optical density of 0.60 at 600 nm prior to inoculation into TSA. Preparation of the spent broth from lactic acid isolates involved adjusting the pH of each broth sample to neutral levels (6.5-7.5). This process eliminated the possible antimicrobial effects of acid on the pathogens. All lactic acid bacterial isolates were challenged with a broad range of pathogens including *Staphylococcus aureus, Salmonella typhimurium, E. coli* K12, *E. coli* F41 (Purdue Univ., Ind.), *E. coli* (Oklahoma State Univ.), *E. coli* K88 (Iowa State Univ.), *E. coli* K99 (Texas A&M University), *E. coli* K88 (Georgia), *E. coli* (Arkansas), and *Clostridium perfringens*.

Forty-one lactic acid isolates were chosen for further screening based on both antimicrobial activity against the broad-range pathogens, and genetic prevalence in Wisconsin and California calves. Eleven pathogens isolated directly from sick calves were chosen for the additional challenge. These pathogens included three strains of *E. coli* (B41, B44, B117) and one strain of *Salmonella typhimurium* (S2a) from Barron, Wis., five strains of *E. coli*, and one strain of *Salmonella* from Missouri, and the ATCC strain 3624 of *Clostridium perfringens*.

B. Results

Following genetic identification, strains were evaluated for their ability to produce antimicrobial activity against common calf microbial pathogens. No strain inhibited all ten of the general, broad-range pathogens tested. However one strain, JD19, inhibited nine pathogens from the broad-range group including strains of *Salmonella typhimurium, Clostridium perfringens*, and seven types of *E. coli*. The number of lactic acid isolates inhibiting general pathogen growth ranged from zero (*S. aureus*) to 312 (*E. coli* F41) (FIG. 6). Growth of *S. typhimurium* was inhibited by 128 isolates, while *E. coli* K12 was inhibited by only 78 isolates. *E. coli* (Oklahoma State Univ.), *E. coli* K88 (Iowa State Univ.), *E. coli* K99 (Texas A&M Univ.), *E. coli* K88 (Georgia), and *E. coli* (Arkansas) were inhibited by 141, 277, 182, 156, and 123 lactic acid isolates respectively.

Forty-one lactic acid isolates, selected for their high genetic prevalence and broad-range pathogen inhibition, were challenged with additional specific calf pathogens in order to maximize the range and specificity of the antimicrobials produced. The growth of several pathogens was not inhibited by any of the lactic acid isolates. These included two strains of *E. coli* from Barron, Wis. (B41 and B117), two strains of *E. coli* from Missouri, and the ATCC strain of *Clostridium perfringens*. Conversely, the growth of two strains of *E. coli* from Missouri was strongly hindered by many of the selected lactic acid isolates. Strain 9-17b was inhibited by 20 isolates, while 24 isolates inhibited pathogen 2-1a. Moreover, lactic acid isolates produced antimicrobial compounds against one strain of *E. coli* (B44) from Barron, Wis. (two isolates), *E. coli* from Missouri (one isolate), and *Salmonella typhimurium* from both Wisconsin (three isolates) and Missouri (four isolates) (FIG. 7). These results were utilized to further narrow the group of potential lactic acid isolates for use in a direct-fed microbial product.

Numerical predominance determined by genotypic prevalence and antimicrobial production against common calf pathogens were both pertinent factors in the final selection of six isolates for use in a direct-fed microbial product (Table 1). The chosen strains, AJ25, HE17, JD19, CI15, DJ6, and ID7, embrace many facets of tract diversity and employ tract heterogeneity. The combination of selected lactic acid bacteria was chosen to provide benefits not only to each intestinal section, but also to every individual host calf in varied environmental regions (different states).

TABLE 1

Characteristics of selected lactic acid bacteria.

| Isolate | State of origin | Intestinal region | Number of pathogens Inhibited | Unique characteristics | Biochemical identification |
|---|---|---|---|---|---|
| AJ25 | WI | jejunum | 11 | Most common WI genotype- visual analysis | *Lactobacillus brevis* |
| HE17 | CA | esophagus | 4 | Most common CA genotype- visual analysis | *Lactobacillus brevis* |
| JD19 | CA | duodenum | 11 | Best antimicrobial producer | *Lactococcus lactis* |
| CI15 | WI | ileum | 6 | Genotype in both WI and CA | *Lactobacillus lactis* |
| DJ6 | WI | jejunum | 9 | Most common WI genotype | *Lactobacillus lactis* |
| ID7 | CA | duodenum | 11 | One most common CA genotype | *Lactococcus lactis* |

Example 3

Animal Trials

A. Materials and Methods

1. General Trial Protocols:

Two experiments (Experiments 1 and 2) were conducted using a randomized complete block design. Holstein bull calves (n=60 per trial) were purchased from an area sale barn and transported to Merrick Animal Nutrition, Inc. Calf Research Farm. On arrival, calves were weighed and assigned to a treatment and hutch depending on the initial weight of the animal. Jugular blood samples were collected and centrifuged for testing serum IgG levels with a Palm Lab (PalmLab, Inc. Newburg, Wis.).

All calves were fed a standard all milk replacer diet. (Gold Star, Merrick's Animal Nutrition, Union Center, Wis.) medicated with Neo-Oxy 100/50 MR (Penn Field Animal Health, Omaha, Nebr.) at 454 g/d reconstituted to 12% DM. Nutrient compositions of final diets are found in Table 2 below. Analyses of final milk replacer diets were completed using approved Association of Analytical Chemists (AOAC) methods.

TABLE 2

Nutrient Composition of Milk Replacer and Calf Starter.

| | Exp. 1 Milk Replacer | Exp. 2 Milk Replacer | Starter |
|---|---|---|---|
| Experiment 1 | | | |
| CP, % | 19.91[a] | 20.84[a] | 18.00[b] |
| Fat, % | 20.72[a] | 20.45[a] | 3.00[b] |
| Crude Fiber, % | 0.09[a] | 0.08[a] | 7.00[b] |
| ADF, % | — | — | 9.00[b] |
| Vitamin A, IU/kg., min | 77,090[b] | 77,090[b] | 22,000[b] |
| Vitamin D-3, IU/kg., min | 16,520[b] | 16,520[b] | 3,744[b] |

TABLE 2-continued

Nutrient Composition of Milk Replacer and Calf Starter.

|  | Exp. 1 Milk Replacer | Exp. 2 Milk Replacer | Starter |
|---|---|---|---|
| Vitamin E, IU/kg., min | 330[b] | 330[b] | 198[b] |
| Direct-fed microbial, cfu/g | 10,000,000,000 | 10,000,000,000 | — |
| Oxytetracycline, mg/kg | 222.00[b] | 222.00[b] | — |
| Neomycin, mg/kg | 444.00[b] | 444.00[b] | — |
| Decoquinate, mg/kg | — | — | 50.00[b] |

[a] = analyzed values;
[b] = formulated values

Calves were assigned to a treatment diet that did (DFM) or did not (CON) contain the direct-fed microbial. The DFM included strains AJ25, HE17, JD19, CI15, DJ6, and ID7. The direct-fed microbial was fed as a freeze-dried water soluble concentrate consisting of 45% active ingredients and 55% carriers (maltrin and dextrose) at a count of $6.5 \times 10^9$ CFU/g. The direct-fed microbial consisted of equal live cell counts of each of the six strains to provide at total of $1 \times 10^{10}$ CFU/animal/day. The freeze-dried bacterial strains and carriers were package (50 g) in foil bags, heat sealed, and stored frozen until used. The entire 50 g bag of the direct-fed microbial pack was added to the liquid milk replacer prepared for 30 calves, allowed to rehydrate, and fed once per day at a 0600 feeding on a daily basis.

Addition of the direct-fed microbial pack to the trial diets began on d 1 of the trial and ended at weaning (d 42). Calves were fed milk replacer in nipple bottles at approximately 0600 and 1700 h daily. A complete pellet commercial calf starter (Kent Feeds, Inc., Muscatine, Iowa) was offered free choice beginning on d 1. Feed refusals were recorded daily. Weaning occurred on d 43 dependent on each calf consuming at least 454 g/d of calf starter for 3 consecutive days. Any calf not consuming sufficient calf starter to be weaned was offered one-half of the usual daily milk replacer feeding per day to encourage starter intake. No direct-fed microbial was fed post-weaning. Water was offered free choice beginning on d 0.

Calves were weighed weekly. When calves required antibiotic treatments they were administered according to trial protocols and recorded daily. Antibiotic treatment was required for calves with severe scours, elevated temperature, respiratory infections and infected navel or joints.

Subjective fecal scores were recorded daily using a scale of 1 to 4, where 1=very firm, 2=normal fecal consistency, 3=watery, 4=extremely watery. A scour day was defined as any day a fecal score of 3 or 4 was recorded. Any calf exhibiting signs of scours was treated twice daily with oral re-hydration therapy using a commercial electrolyte solution manufactured without direct-fed microbial (Blue Ribbon Calf Electrolytes, Merrick Animal Nutrition, Union Center, Wis.). Oral re-hydration therapy continued until 1 d after signs of scours abated. Milk replacer feedings were unchanged during administration of electrolyte therapy.

2. Statistical Analysis:

Weights, fecal scores, and daily calf starter intakes were summarized by week. These data were then analyzed using the general linear model procedure of Systat (1998). Means were separated using Fisher's Least Square difference and data were contrasted between treatments. Data for percent calves weaned at d 43, percent calves scoured and percent calves treated, were analyzed using Pearson's Chi-Square (Systat Version 8.0, 1998). Significance was declared at $P<0.05$ with trends reported at $P<0.10$. Experimental data for each trial were analyzed separately due to treatment by trial interactions.

B. Results

1. Experiment 1:

Results of Experiment 1 are shown in Table 3. Beginning on d 14, calves fed the direct-fed microbial had significantly ($P<0.05$) greater average weekly weights (FIG. 8). This difference was evident through d 42 at which time calves fed the direct-fed microbial (DFM) were on average 2.98 kg heavier than calves fed the CON diet. At d 56, calves fed the DFM maintained an average 3.22 kg weight difference greater than the calves fed the CON diet (P=0.15). Average daily gains at d 42 were significantly (P=0.04) greater for calves fed the DFM than for those calves fed the CON diet (0.47 vs. 0.39 kg/d for the DFM and CON diets, respectively). Significant differences in average weekly starter intake and gain:feed ratios were observed and are shown in FIGS. 9 and 10.

TABLE 3

Effect of feeding a novel direct-fed microbial on calf performance for Experiment 1.

|  | Diet | | | |
|---|---|---|---|---|
|  | CON | DFM | SE | P-Value |
| N | 28 | 29 | | |
| Total Serum Protein, mg/ml | 4.47 | 3.25 | 0.51 | 0.09 |
| BW,[1] kg | | | | |
| d 0 | 43.54 | 43.45 | 0.15 | 0.74 |
| d 42 | 60.04 | 63.02 | 1.02 | 0.04 |
| d 56 | 70.10 | 73.32 | 1.53 | 0.15 |
| Total Weight Gain | 26.56 | 29.83 | 1.53 | 0.14 |
| ADG, kg/d | | | | |
| d 0-42 | 0.39 | 0.47 | 0.02 | 0.04 |
| d 0-56 | 0.47 | 0.53 | 0.03 | 0.14 |
| Total Starter Intake, kg | 44.81 | 47.26 | 2.61 | 0.21 |
| Gain: Feed | 0.21 | 0.21 | 0.07 | 0.62 |
| Weaned, % | 93 | 90 | | 0.67 |
| Calves Scouring, % | 39 | 28 | — | 0.35 |
| Calves Treated, % | 43 | 34 | — | 0.52 |

[1]BW is body weight

The initial health status of these calves, as indicated by the serum IgG level, was poor (3.25 and 4.47 mg/ml of serum IgG for calves on the direct-fed microbial and CON diets respectively). Only 3.5% of all Experiment 1 calves did not have failure of passive transfer (<10 mg/ml of serum IgG). Mortality was not significantly different between groups (3.3% and 6.7% for calves fed the DFM and CON diets, respectively).

For calves fed the direct-fed microbial diet there was a 28.2% reduction in the number of calves scouring over the calves fed the CON diet.

2. Experiment 2:

Results of Experiment 2 are shown in Table 4. Calves fed both the DFM and CON diet exhibited similar average weekly weight gains, total weight gains, average daily gain (ADG), and gain:feed, with no significant differences reported. Average weekly starter intakes and total starter intakes were not significantly different.

TABLE 4

Effect of feeding a novel direct-fed microbial on calf performance for Experiment 2.

|  | Diet | | | |
| --- | --- | --- | --- | --- |
|  | CON | DFM | SE | P-Value |
| N | 29 | 28 |  |  |
| Total Serum Protein, mg/ml | 8.69 | 7.44 | 1.62 | 0.59 |
| BW, kg |  |  |  |  |
| d 0 | 43.07 | 43.14 | 0.21 | 0.81 |
| d 42 | 63.31 | 63.17 | 1.24 | 0.94 |
| d 56 | 75.00 | 74.55 | 1.73 | 0.89 |
| Total Weight Gain | 31.92 | 31.51 | 1.71 | 0.88 |
| ADG, kg/d |  |  |  |  |
| d 0-42 | 0.48 | 0.48 | 0.03 | 0.90 |
| d 0-56 | 0.57 | 0.56 | 0.03 | 0.87 |
| Total Starter Intake, kg | 50.98 | 47.94 | 2.90 | 0.46 |
| Gain: Feed | 0.22 | 0.23 | 0.01 | 0.31 |
| Weaned at d 43, % | 97 | 100 | — | 0.32 |
| Calves Scouring, % | 41 | 18 | — | 0.05 |
| Calves Treated, % | 31 | 46 | — | 0.23 |

Serum IgG levels for calves on Experiment 2 were twice those of calves on Experiment 1 (7.44 and 8.69 mg/ml of serum IgG for calves on the direct-fed microbial and CON diets respectively). Mortality was not significantly different between groups (6.7% and 3.3% for calves fed the DFM and CON diets, respectively).

For calves fed the DFM diet there was a 56.1% reduction in calves scouring during the trial (18% of calves fed the direct-fed microbial diet and 41% of calves fed the CON diet, P=0.05). Calves fed the DFM diet did show a greater percent of calves being treated with antibiotics (15% more calves). However, these treatments were mostly for respiratory and joint infections.

C. Discussion

Results of Experiments 1 and 2 indicate that the novel direct-fed microbial used in this study is beneficial to the calf by reducing scours and promoting growth. In both Experiments 1 and 2, the percent of calves having at least one scours incident decreased by 28.2% in Experiment 1, P=0.35 and 56.1% in Experiment 2, P=0.05. These results are greater than those reported by previous researchers who studied direct-fed microbials (Abe, et al., 1995; Bechman, et al., 1977).

Although calves fed the DFM diet in Experiment 1 had significantly greater ADG average weekly weights, intakes, and feed efficiency, there were no differences in performance for the DFM and CON treatments in Experiment 2. These conflicting results are similar to those reported previously where calves fed a direct-fed microbial did (Abe, et al., 1995; Christen, et al., 1995; Schwab, et al., 1980) or did not (Cruywagen, et al., 1996; Jenny et al., 1991; Morrill, et al., 1995) exhibit improved growth.

Because calves in Experiment 1 arrived at the research farm with significantly (P<0.10) lower serum IgG levels (3.9 vs. 7.9 mg/ml for all calves in Experiment 1 and Experiment 2 respectively), than calves in Experiment 2, the lack of performance difference in Experiment 2 can be attributed to the superior initial health status of these calves and thus a lower stress level. Ruppert, et al. (1994) observed similar results in calves raised in relatively stress-free versus less than optimal environmental conditions.

These experiments indicate that administering the direct-fed microbial to calves reduces the percentage of calves scouring and improves performance for calves, especially for calves with a poor initial health status.

Further, due to the similarities between calves and other animals, treatment of other animals using lactic acid bacteria in a manner similar to those illustrated in the above experiments should result in similar benefits for those types of animals as well.

Example 4

This experiment was run to determine the effect of three levels of a direct-fed microbial made in accordance with the invention on calf performance for calves fed a conventional feeding system.

A. Materials and Methods

1. Direct-Fed Microbial:

Calves were separated into four treatment groups with 15 calves each. The direct-fed microbial (DFM) fed in this trial was prepared in the same manner as the DFM in Example 3. That is, the DFM included strains AJ25, HE17, JD19, CI15, DJ6, and ID7. The direct-fed microbial was fed as a freeze-dried water soluble concentrate consisting of 45% active ingredients and 55% carriers (maltrin and dextrose) at a count of $6.5 \times 10^9$ CFU/g. The direct-fed microbial consisted of equal live cell counts of each of the six strains. The freeze-dried bacterial strains and carriers were package (50 g) in foil bags, heat sealed, and stored frozen until used.

Calves in treatment A (con) were not fed any DFM and served as a control. Calves in treatment B (low) received a low level of the DFM ($1 \times 10^9$ cfu/g); calves in treatment C (med) received a mid level of the DFM ($5 \times 10^9$ cfu/g); and calves in treatment D (high) received a high level of the DFM ($1 \times 10^{10}$ cfu/g).

Calves in treatments B, C and D were fed from d 1 through d 42 and were fed at 1 g of the DFM per head per day. The DMF was added to morning milk replacer feeding. The milk replacer included 20% Protein, 20% Fat (Gold Star, Merrick's, Inc., Middleton, Wis.). Calves were fed the milk replace at the rate of 1 lb. (454 g) per day for 42 days. The milk replacer was medicated with Neo-Terramycin (400/200). Calves were weaned dependent on eating 1 lb. of calf starter (Active Starter 18DQ, complete pellet, Kent Feeds, Muscatine, Iowa) per day for a minimum of 3 consecutive days. The calf starter, which was medicated with decoquinate, was offered ad libitum from d 1 to d 56. Calf starter intake was measured daily. Water was offered ad libitum from d 0 to d 56.

Weights were obtained weekly. Serum IgG obtained on d 0. Fecal scores were recorded daily. Heath treatments were recorded daily.

2. Statistics

Because four levels of DFM were utilized in this trial, linear and quadratic significance was evaluated. Linear significance indicates that the variable either increases or decreases as the DFM dose increases. Quadratic significance indicates that the treatments receiving the mid-level of DFM would be higher than either the control or the high dose. Significance was declared at P<0.05 with trends reported at P<0.10.

B. Results

Because of the low number of calves per treatment, standard errors were higher than normal for this trial. Beginning at d 14 and continuing until d 35, calves fed the high level of DFM were significantly heavier than calves fed the control (P<0.05) as well low and med (P<0.10) levels of DFM. During this time period, linear significance (P<0.05) was also observed. This trend continued through the remainder of the trial, but was not significant. At the end of the trial, calves fed the high level of DFM were on average 7.4 pounds greater than calves fed the control diet. At day 56 weights for each treatment were control—155.0 lb., low—154.9 lb., med—156.7 lb., and high—162.4 lb.

From weeks 0 through 3, calves fed the high level of DFM grew at a significantly (P<0.05) greater ADG than calves fed the control diet (0.489 vs. 0.778 pounds per day for control and high level treatments respectively). Calves fed the low and med levels of DFM were intermediate. During weeks 1 through 3, there was also a linear significance (P=0.028) in ADG such that as the DFM dose increased, ADG increased. At the end of 6 weeks and the end of 8 weeks, although there was no significant difference, calves fed the high level of DFM has greater ADG than all other treatments.

Although the total weight gain was not significantly different between groups, calves fed the high level of DFM had the greatest amount of total gain compared to all other treatments. Total weight gains for each treatment were control—52.9 lbs., low—52.2 lbs., med.—54.9 lbs., and high—58.7 lbs.

Standard errors for these data were higher than normal due to the low number of calves per treatment. Calves fed the high level of DFM had consistently greater average weekly feed intakes during the entire trial. During weeks 1 through 4, this was a significant difference. A statistically significant linear difference also existed for the first 3 weeks of the trial (P=0.09 for weeks 1 and P<0.05 for weeks 2 and 3).

Although total starter intake was not significantly different, calves fed the high levels of DFM ate 14 to 16 pounds more starter than any other treatment. Total starter intakes for each treatment were control—88.3 lbs., low—86.3 lbs., med.—87.1 lbs., and high—102.3 lbs.

Feed efficiencies for weeks 1 through 3 were significantly greater (P<0.05) for calves fed the high level of DFM compared to the control diet. Calves fed the low and med levels of DFM were intermediate. During weeks 4 through 6, calves fed the control diet had the greatest feed efficiency and showed a trend (P<0.10) towards having a greater feed efficiency than calves fed the med level of DFM. The low and high treatments were intermediate. For the entire trial feed efficiencies were identical for all treatments.

No statistical differences were evident for the percent calves weaned at day 42. The percent of calves weaned for each treatment were control—80.0%, low—86.7%, med—80.0%, and high—92.3%.

There were no statistical differences in the percent calves that died on each treatment. On Treatment A (control), 0/15 (0%) calves died; On Treatment B (low), 0/15 (0%) calves died; On Treatment C (med), 0/15 (0%) calves died; and On Treatment D (high), 2/15 (13.3%) calves died, with one of the calves dying from *E. coli* enteritis. Overall mortality was 3.3%, which is excellent.

No significant differences in initial serum IgG levels existed between the groups of calves. Serum IgG levels were higher than those normally observed. Initial serum IgG levels for each treatment were control—12.1 mg/ml, low—9.1 mg/ml, med—11.0 mg/ml, and high—9.3 mg/ml.

The percent of calves with Failure of Passive Transfer (FPT) was not different between treatment groups. The percent of calves with FPT for each treatment were control—46.7%, low—73.3%, med—60.0%, and high—61.5%.

Although some differences if weekly fecal scores did exist, average fecal scores were never over 2.5 with a 2 considered normal. Overall, there was little difference in average weekly fecal scores for each treatment.

There were no significant differences in the percentage of calves scouring. Calves fed the high level of DFM had 18.5% fewer calves scouring than the control calves. The percentage of calves scouring on each treatment were control—80.0%, low—66.7%, med—80.0%, and high—61.5%

Although the percentage of calves treated for all illnesses was not significant, calves on the high level of DFM had 10.8% fewer calves treated with antibiotics. No calves fed the high level of DFM were treated with antibiotics for scours. Thus, only the use of the DFM and electrolytes were needed to combat scours incidence. Additionally, although not significant, when any level of DFM was fed, the percentage of calves treated with antibiotics for respiratory illness was decreased. Results are shown in Table 5.

TABLE 5

| Illness | Control | Low | Med | High | P |
|---|---|---|---|---|---|
| ALL CALVES TREATED | 80.0% | 80.0% | 73.3% | 62.2% | 0.886 |
| Scours | 13.3% | 0.0% | 20.0% | 0.0% | 0.137 |
| Respiratory | 53.3% | 66.7% | 53.3% | 30.8% | 0.301 |
| Elevated Temperature | 66.7% | 26.7% | 26.7% | 0.0% | 0.106 |
| Blood in feces | 13.3% | 20.0% | 66.7% | 30.8% | 0.379 |
| Other | 19.0% | 22.2% | 15.9% | 14.6% | 0.797 |

There were no differences in the feed (Calf Starter) cost per pound of gain. The differences in treatment cost (includes antibiotics as well as electrolytes) were not statistically significant; however, calves fed the high level of DFM averaged $2.46 less per calf to treat. Calves fed the low and med levels of DFM had the greatest total cost of treatments. The average cost of treating each calf per treatment were control—$11.88, low—$14.62, med—$14.21, and high—$9.43.

There were no statistical differences in the average cost of treating scours, which included all treatments related to an incidence of scours. It should be noted that this is different from the percentage of calves that were treated with antibiotics for scours, as electrolytes are the most expensive treatment for scours that are used at the farm.

Although there were no statistical differences, the cost of treating calves with respiratory illness, which includes all treatments related to respiratory ill, was $2.35 less per calf to treat for calves fed the high level of DFM when compared to the calves fed the control diet. The average cost of treating each calf per treatment were control—$4.10, low—$6.07, med—$5.91, and high—$1.75.

In summary, calves fed the high level of DFM had 18.5% fewer (80.0% vs. 61.5% for the control and high treatments respectively) calves scour than calves fed the control treatment (66.7% and 80.0% of calves fed the low and med levels of DFM scoured, respectively). The percentage of calves needing antibiotics to recover from scours was lower for calves fed the high level of DFM compared to the control calves. However, calves fed the med level of DFM had the highest percentage of calves that needed antibiotics to recover from a scours incidence. Calves fed the high level of DFM were $2.46 less expensive per calf to treat with antibiotics than control calves. However, calves fed the low and med level diets were higher than expected.

Calves fed the high level of DFM were 7.4 pounds heavier than calves fed the control diet at the end of the trial (155.0, 154.9, 156.7 and 162.4 pounds for the control, low, med and high treatments respectively). Of the four levels of DFM fed in this trial (no DFM, low, med and high), those calves fed the high level performed better than all other treatments for health and performance related variables.

Example 5

This experiment was run to determine the feeding rate of the direct fed microbial (DFM) by optimizing performance and health of calves.

A. Materials and Methods

Calves were separated into four treatment groups with 15 calves each. The direct-fed microbial (DFM) fed in this trial was prepared in the same manner as the DFM in Example 4. The treatment groups were established as in Example 4. The calves receiving the DFM (Treatments B, C and D) were fed the same days and amounts as in Example 4. The DFM was added to morning milk replacer feeding, as in Example 4. The milk replacer and water offerings were as described in Example 4.

Weights were obtained weekly. Serum IgG was obtained on d 0. Fecal scores were recorded daily. Heath treatments were recorded daily. The statistics were performed as described in Example 4. The diet formulation and Treatment Nutrient Analysis were the same as in Example 4.

B. Results

Because of the low number of calves per treatment, standard errors were higher than normal for this trial. Beginning on d 21, calves fed the med level of DFM had the greatest weight gain, with calves fed the high level weighing slightly less, and the calves on the control and low treatments having the lowest weights.

Calves fed the med level of DFM were significantly heavier than the control calves at d 42 ($P<0.05$), d 49 ($P<0.05$) and d 56 ($P<0.10$). At the end of the trial, calves fed the med level of DFM were on average 9.4 pounds greater than calves fed the control diet, and calves fed the high level of DFM were 4.74 pounds heavier than calves fed the control diet. At day 56 weights for each treatment were control—151.3, low—153.8, med—160.7 and high—156.0.

Calves fed the med level of DFM had the greatest ADG during the trial at all time points measured. These differences were significant for weeks 4 though 6, weeks 0 through 6 and throughout the entire trial when compared with ADG for the control and low treatment levels. Calves fed the high level of DFM were slightly lower in ADG than the med treatment level. Calves fed the control diet consistently had the lowest ADG.

Although the total weight gain was not significantly different between groups, calves fed the med level of DFM had the greatest amount of total gain compared to all other treatments. Total weight gains for each treatment were control—50.1 lbs., low—51.9 lbs., med.—59.2 lbs., and high—54.5 lbs.

Standard errors for these data were higher than normal due to the low number of calves per treatment. Calves fed the med level of DFM had consistently greater average weekly feed intakes during the entire trial. During weeks 6 through 8, this was a significant difference when compared to the Control diet.

Calves fed the med level of DFM ate a significantly ($P<0.10$) greater amount of starter than calves fed the control diet. The low and high treatment levels had intermediate starter intakes. Total starter intakes for each treatment were control—89.2 lbs., low—95.7 lbs., med.—106.7 lbs., and high—95.2 lbs.

There were no significant differences in feed efficiencies for any of the time periods evaluated. No statistical differences were evident for the percent calves weaned at day 42. The percent of calves weaned for each treatment were control—84.6%, low—93.3%, med—100%, and high—100%.

There were no statistical differences in the percent calves that died on each treatment. For Treatment A (control), 2/15 (13.3%) calves died, with one of these dying from Clostridial enteritis. For Treatment B (low), 0/15 (0%) calves died. For Treatment C (med), 0/15 (0%) calves died. For Treatment D (high), 1/15 (6.7%) calves died from a congenital heart defect (enlarged heart). Overall mortality was 5.0%, which is excellent No significant differences in initial serum IgG levels existed. Initial serum IgG levels for each treatment were control—7.7 mg/ml, low—8.9 mg/ml, med—5.6 mg/ml, and high—6.7 mg/ml.

The percent of calves with Failure of Passive Transfer (FPT) was not different between treatment groups. The percent of calves with FPT for each treatment were control—69.2%, low—80.0%, med—93.3%, and high—85.7%.

Although some differences of weekly fecal scores did exist, average fecal scores were never over 2.5 with a 2 considered normal. Overall, there was little difference in average weekly fecal scores for each treatment.

There were no significant differences in the percentage of calves scouring. Calves fed the high level of DFM had 20.3% fewer calves scouring than the control calves. The percentage of calves scouring on each treatment were control—84.6%, low—86.7%, med—73.3% and high—64.3%.

There were no differences in the percentage of calves treated with antibiotics. Calves fed the low level of DFM had the lowest percentage of calves that scoured. No calves fed the high or low levels of DFM were treated with antibiotics for scours. Thus, only the use of the DFM and electrolytes were needed to combat scours incidence. Results are shown in Table 6.

TABLE 6

| Illness | Control | Low | Med | High | P |
|---|---|---|---|---|---|
| ALL CALVES TREATED | 69.2% | 46.7% | 73.3% | 64.3% | 0.452 |
| Scours | 7.7% | 0.0% | 20.0% | 0.0% | 0.108 |
| Respiratory | 46.2% | 20.0% | 46.7% | 50.0% | 0.314 |
| Elevated Temperature | 23.1% | 6.7% | 6.7% | 14.3% | 0.506 |
| Blood in feces | 23.1% | 20.0% | 13.3% | 35.7% | 0.540 |
| Other | 7.7% | 26.7% | 20.0% | 0.0% | 0.161 |

There were no differences in the feed (calf starter) cost per pound of gain. Although differences were not statistically significant, calves fed the high level of DFM had the lowest average treatment cost (includes antibiotics as well as electrolytes) and averaged $1.87 less per calf to treat than those calves fed the control diet. Calves fed the med level of DFM had the greatest total cost of treatments. The average cost of treating each calf per treatment were control—$8.99, low—$8.58, med—$9.66, and high—$7.12.

There were no statistical differences in the average cost of treating scours (includes all treatments related to an incidence of scours). Calves fed the low level of DFM had the highest cost of treating scours followed by the med, control and high levels.

There were no significant differences in the cost of treating respiratory illness (includes all treatments related to respiratory illness). Calves fed the control diet had the highest cost, while calves fed the low level of DFM had the least cost ($4.32 difference). Calves fed the med and high levels of DFM were intermediate in their cost of treating respiratory illness. The average cost of treating each calf per treatment were control—$6.12, low—$1.80, med—$2.70, and high—$4.91.

In summary, calves fed the med level of DFM were 9.4 pounds heavier than the calves fed the control diet. Calves fed the high level were 4.7 pounds heavier than the control diet. Ending weights for the trial were 151.3, 153.8, 160.7, and 156.0 pounds for the control, low, med and high treatments, respectively. Calves fed the high level of DFM had 20.3% fewer (84.6% vs. 64.3% for the control and high treatments, respectively) calves scour than calves fed the control treatment (86.7% and 73.3% of calves fed the low and med levels of DFM scoured, respectively). The percentage of calves needing antibiotics to recover from scours was lower for calves fed the high and low level of DFM compared to the control and med calves, as the high and low treatment groups had no calves treated with antibiotics due to scouring. Calves fed the med level of DFM had the highest percentage of calves that needed antibiotics to recover from a scours incidence. Calves fed the high level of DFM were $1.87 less expensive per calf to treat with antibiotics than control calves. Of the four levels of DFM fed in this trial (no DFM, low, med and high), those calves fed the med level had the greatest weight gains while calves fed the high level of DFM exhibited better overall health characteristics.

It is understood that the various preferred embodiments and examples are shown and described above to illustrate different possible features of the invention and the varying ways in which these features may be combined. Apart from combining the different features of the above embodiments in varying ways, other modifications are also considered to be within the scope of the invention. The invention is not intended to be limited to the preferred embodiments described above, but rather is intended to be limited only by the claims set out below. Thus, the invention encompasses all alternate embodiments that fall literally or equivalently within the scope of these claims.

BIBLIOGRAPHY

Abe, F., N. Ishibashi and S. Shimamauru. 1995. Effect of administration of Bifidobacteria and Lactic Acid bacteria to newborn calves and piglets. J. Dairy Sci. 78:2838-2846.

Bechman, T. J., J. V. Chambers, and M. D. Cunningham. 1977. Influence of *Lactobacillus acidophilus* on the performance of young dairy calves. J. Dairy Sci. 60 (Suppl. 1):74. (Abstr.).

Christen, S. D., K. Wardwell, T. M. Hill, and L. D. Roth. 1995. The effect of direct-fed microbials on the performance of pre-weaned Holstein calves. J. Anim. Sci. 73 (Suppl. 1): 249 (Abstr.).

Cruywagen, C. W., I. Jordaan, and L. Venter. 1996. Effect of *Lactobacillus acidophilus* supplementation of milk replacer on preweaning performance of calves. J. Dairy Sci. 79:483-486.

Jenny, B. F., H. J. Vandijk, and J. A. Collins. 1991. Performance and fecal flora of calves fed a *Bacillus subtilis* concentrate. J. Dairy Sci. 74:1968-1973.

Morrill, J. L., J. M. Morrill, A. M. Feyerherm, and J. F. Laster. 1995. Plasma proteins and a probiotic as ingredients in milk replacer. J. Dairy Sci. 78:902-907.

Ruppert, L. D., G. C. McCoy and M. F. Hutjens. 1994. Feeding of probiotics to calves. J. Anim. Sci. 72 (Suppl. 1): 296 (Abstr.).

Systat 8.0 Statistics. 1998. SPSS Inc. Chicago, Ill.

Tomkins, T., J. Sowinski, and J. K. Drackley. 1994. Milk replacer research leads to new developments. *Feedstuffs* 66(42):13-23.

USDA National Animal Health Monitoring System. 2002. Dairy 2002 Part 1: Reference of dairy health and management in the United States, 2002.

VanHorn, H. H. and C. J. Wilcox. 1992. Large Dairy Herd Management. American Dairy Science Association, Champaign, Ill.

What is claimed is:

1. A biologically pure culture of a *Lactococous lactis* strain having all of the identifying characteristics of the *Lactococous lactis* strain ATCC PTA-6104.

2. A biiologically pure culture of *Lactococous lactis* strain ATCC PTA-6104.

3. A method of making a direct-fed microbial, the method comprising:
   (a) growing, in a liquid nutrient broth, the biologically pure culture of claim 2; and
   (b) separating the biologically pure culture of step (a) from the liquid nutrient broth to provide for the direct-fed microbial.

4. The method of claim 3, further comprising freeze drying the biologically pure culture.

5. The method of claim 4, further comprising adding the freeze-dried biologically pure culture to a carrier.

6. A composition comprising biologically pure cultures of *Lactococous lactis* strain ATCC PTA-6104, *Lactobacillus brevis* strain ATCC PTA-6099, *Lactobacillus brevis* strain ATCC PTA-6100, *Lactobacillus lactis* strain ATCC PTA-6101, *Lactobacillus lactis* strain ATCC PTA-6102, and *Lactococcus lactis* strain ATCC PTA-6103.

7. A method of treating an animal, the method comprising administering to the animal an effective amount of the composition of claim 6, wherein the composition is suitable for administration to animals, and wherein upon administration to an animal, the composition provides at least one of the following (a) improves performance in the animal and (b) reduces scours in the animal, and wherein the animal is selected from the group consisting of cows, cattle, calves, sheep, pigs, deer, goats and elk.

8. The method of claim 7, wherein the animal is a calf having a decreased initial health status, and wherein after about 42 days of feeding the composition performance is improved by at least about 15%.

9. The method of claim 8, wherein the performance is improved by at least about 25%.

10. The method of claim 7, wherein the animal is a calf, and wherein after about 42 days of feeding the composition to the calf, scours in the calf is reduced by at least about 15%.

11. The method of claim 10, wherein the scours is reduced by at least about 25%.

12. The method of claim 11, wherein the scours is reduced by at least about 50%.

13. A method of claim 7, wherein the composition is administered to the animal at a level such that the animal is dosed daily with about $1 \times 10^9$ CFU/animal/day to about $5 \times 10^{10}$ CFU/animal/day.

14. A method of claim 13, wherein the composition is administered to the animal at a level such that the animal is dosed daily with about $1 \times 10^{10}$ CFU/animal/day.

15. A method of claim 7, wherein the animal is a calf, and wherein the composition is administered to the calf from about birth to about six weeks of age.

16. A method of claim 7, wherein the animal is a calf, and wherein the composition is administered to the calf in a calf milk replacer.

17. A composition comprising:
(a) a biologically pure culture of *Lactococous lactis* strain ATCC PTA-6104; and
(b) at least one biologically pure culture selected from *Lactobacillus brevis* strain ATCC PTA-6099, *Lactobacillus brevis* strain ATCC PTA-6100, *Lactobacillus lactis* strain ATCC PTA-6101, *Lactobacillus lactis* strain ATCC PTA-6102, and *Lactococcus lactis* strain ATCC PTA-6103.

* * * * *